United States Patent
Adam et al.

(10) Patent No.: US 9,556,134 B2
(45) Date of Patent: Jan. 31, 2017

(54) HUMIC ACID DERIVATIVES AND METHODS OF PREPARATION AND USE

(71) Applicant: EMPIRE TECHNOLOGY DEVELOPMENT LLC, Wilmington, DE (US)

(72) Inventors: Georgius Abidal Adam, Edensor Park (AU); Anita Needham, Mangerton (AU)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/894,660

(22) PCT Filed: May 28, 2013

(86) PCT No.: PCT/US2013/042814
§ 371 (c)(1),
(2) Date: Nov. 30, 2015

(87) PCT Pub. No.: WO2014/193338
PCT Pub. Date: Dec. 4, 2014

(65) Prior Publication Data
US 2016/0108010 A1    Apr. 21, 2016

(51) Int. Cl.
| C07D 413/14 | (2006.01) |
| C07D 307/91 | (2006.01) |
| C07D 307/77 | (2006.01) |
| C07D 265/38 | (2006.01) |

(52) U.S. Cl.
CPC ........... C07D 265/38 (2013.01); C07D 307/77 (2013.01); C07D 307/91 (2013.01); C07D 413/14 (2013.01)

(58) Field of Classification Search
CPC .................................................. C07D 413/14
USPC ....................................................... 544/102
See application file for complete search history.

(56) References Cited

U.S. PATENT DOCUMENTS

| 4,671,883 | A | 6/1987 | Connell et al. |
| 5,034,045 | A | 7/1991 | Alexander |
| 5,463,129 | A | 10/1995 | Lysenko et al. |
| 7,192,455 | B2 | 3/2007 | Plos et al. |
| 8,211,558 | B2 | 7/2012 | Yoshimura |
| 2004/0115334 | A1 | 6/2004 | Romero Olmedo |
| 2005/0069974 | A1 | 3/2005 | Gladkov et al. |
| 2006/0058566 | A1 | 3/2006 | Shulgin et al. |
| 2006/0286046 | A1 | 12/2006 | Haber |
| 2010/0035887 | A1 | 2/2010 | Ricciardi |
| 2010/0119653 | A1 | 5/2010 | Hall |
| 2011/0031188 | A1 | 2/2011 | Perminova et al. |
| 2011/0111066 | A1 | 5/2011 | Ferguson et al. |

FOREIGN PATENT DOCUMENTS

| CN | 102432306 A | 5/2012 |
| CN | 102863687 A | 1/2013 |
| JP | S58173138 A | 10/1983 |
| JP | 2009298727 A | 12/2009 |
| WO | 9965702 A1 | 12/1999 |
| WO | 2005118511 A2 | 12/2005 |
| WO | 2014193337 A1 | 12/2014 |

OTHER PUBLICATIONS

International Search Report and Written Opinion for International application No. PCT/US2013/042814, mailed on Jan. 31, 2014.
06/01716 Investigations of Humic Acid N with X-ray Photoelectron Spectroscopy: Effect of Acid Hydrolysis and Comparison with 15N Cross Polarization/Magic Angle Spinning Nuclear Magnetic Resonance Spectroscopy, International Atomic Energy Agency. Technical Report Series, International Atomic Energy Agency, Vienna, AT (Jul. 2006), 47(4) p. 263.
Supplementary European Search Report issued in EP13885836.0 dated Feb. 17, 2016.
BHT Product Description, Wholesale Nutrition, accessed at https://web.archive.org/web/20130509093835/http://www.nutri.com/index.cfm/product/31_17/bht.cfm accessed on Mar. 15, 2016, pp. 2.
BioAg Fulvic & Humic Solutions, accessed at https://web.archive.org/web/20120621081858/http://www.bioag.com/teamfulvic/fulvicresearch.html accessed on Mar. 15, 2016, pp. 3.
Folic acid fact sheet, epublications accessed at https://web.archive.org/web/20130429034307/http://www.womenshealth.gov/publications/our-publications/fact-sheet/folic-acid.html    content    last updated Jul. 16, 2012, pp. 6.
Fulvic Acid A Substance Critical to Human Health, accessed at http://web.archive.org/web/20110910224221/http://www.realrawfood.com/sites/default/files/article/Fulvic%20Acid%20Report.pdf accessed on Dec. 11, 2015, pp. 48.
Fulvic Acid Benefits, accessed at https://web.archive.org/web/20130525140616/http://www.supremefulvic.com/documents/html/fulvic_acid.php, accessed on Mar. 15, 2016, pp. 22.
Fulvic acid the miracle molecule, Supremefulvic.com accessed at https://web.archive.org/web/20120329231513/http://www.supremefulvic.com/documents/pdf/8.fulvic.acid.report.pdf accessed on Mar. 15, 2016, pp. 44.
Fulvic acid, Encyclopedia Britannica accessed at http://www.britannica.com/science/fulvic-acid accessed on Mar. 15, 2016, pp. 2.
Global Trends in Polymer Additives, accessed at http://www.plastemart.com/Plastic-Technical-Article.asp?LiteratureID=1514&Paper=global-trends-in-polymer-additives, Oct. 29, 2010, pp. 2.
How You Rot & Rust, accessed at https://web.archive.org/web/20130302050256/http://biomedx.com/microscopes/rrintro/rr1.html, accessed on Mar. 15, 2016, pp. 1.

(Continued)

*Primary Examiner* — Kahsay Habte
(74) *Attorney, Agent, or Firm* — Pepper Hamilton LLP

(57) ABSTRACT

Disclosed are antioxidative natural compounds, their salts, chelates and cleavage derivatives that exhibit a superior combination of properties. The compounds can be used for a variety of purposes, including the stabilization of polymers. The compounds can be prepared by substantially cleaving a humic acid of formula I followed by esterification to provide at least one antioxidant compounds of formula V, formula VI, formula VII, formula VIII, salts thereof, or chelates thereof.

16 Claims, No Drawings

(56) References Cited

OTHER PUBLICATIONS

Humic & Fulvic Acids:The Black Gold of Agriculture, accessed at http://web.archive.org/web/20120417060303/http://www.humintech.com/pdf/humicfulvicacids.pdf accessed on Mar. 15, 2016, pp. 10.
Humic & Fulvic Substances I, Supremefulvic.com accessed at http://www.supremefulvic.com/documents/pdf/2.about.humic-fulvic.substances.1.pdf, accessed on Mar. 15, 2016, pp. 35.
Humic & Fulvic Substances II, Supremefulvic.com accessed at https://www.supremefulvic.com/documents/pdf/3.about.humic-fulvic.substances.2.pdf, accessed on Mar. 15, 2016, pp. 38.
It's Perfectly Clear the Case Against PVC Packaging, Masspirg, accessed at https://web.archive.org/web/20050305121509/http://www.pirg.org/masspirg/enviro/sw/pvc/, accessed on Mar. 15, 2016, pp. 2.
List of food additives, accessed at http://web.archive.org/web/20130424122000/http://en.wikipedia.org/wiki/List_of_food_additives last modified on Mar. 3, 2013, pp. 15.
PH and Acidosis, Supremefulvic.com accessed at https://web.archive.org/web/20090922095505/http://www.supremefulvic.com/documents/html/pHbyDrLam.html, accessed on Mar. 15, 2016, pp. 5.
PH and cancer, accessed at http://www.supremefulvic.com/documents/pdf/11.ph.and.cancer.pdf, accessed on Mar. 15, 2016, pp. 3.
Root of All Disease, Supremefulvic.com accessed at http://www.supremefulvic.com/documents/pdf/7.the.root.of.all.disease(edited).pdf, accessed on Mar. 15, 2016, pp. 19.
The pH Reguatory System of the Body, accessed at http://www.supremefulvic.com/documents/pdf/10.how.you.rot.and.rust.pdf, accessed on Mar. 15, 2016, pp. 28.
Vitamin C in Food Processing, accessed at http://web.archive.org/web/20120916175528/http://www.mratcliffe.com/images/vcb.pdf accessed on Mar. 15, 2016, pp. 5.
What Is Fulvic Acid?, Supremefulvic.com accessed at https://web.archive.org/web/20150319160405/http://www.supremefulvic.com/documents/pdf/1.what.is.fulvic.acid.pdf accessed on Mar. 15, 2016, pp. 17.
Adam et al., Humic substances as new stabilisers for polyvinylchloride, Thermochima Acta (Mar. 1, 1986), (99) pp. 217-222.
Aeschbarer et al., Antioxidant properties of humic substance, Environmental Science and Technology (Jan. 1, 2012), 46(9) pp. 4916-4925.
Aguilar et al., Chromium(III)-, iron(II)- and selenium-humic acid/fulvic acid chelate and supplemented humifulvate added for nutritional purposes to food supplements, The EFSA Journal (Jun. 5, 2009), (1147) pp. 1-36.
Avvakumova et al., Antioxidant Properties of Humic Substances Isolated Form Peloids, Pharmaceutical Chemistry Journal (Mar. 2011), 45(3) pp. 192-193.
Babler et al., Reductive cleavage versus hydrogenation of allyl aryl ethers and allylic esters using sodium borohydride/catalytic ruthenium(III) in various aqueous solvent mixtures, Tetrahedron Letters (Feb. 16, 2011), 52(7) pp. 745-748.
Badary et al., Thymoquinone is a potent superoxide anion scavenger, Drug & Chemical Toxicology (May 2003), 26(2) pp. 87-98.
Bernard et al., Dealkylation of Activated Alkyl Aryl Ethers Using Lithium Chloride in Dimethylformamide, Synthesis (Apr. 1989), 1989(4) pp. 287-289.
Bisig, Plasticizer Market Update, BASF Corporation (Jul. 19-21, 2009), pp. 20.
D'Arcgivio et al., Polyphenols, dietary sources and bioavailablility, Ann 1st Super Sanita (2007), 43(4) pp. 348-361.
Densley, Plasticisers in our food &&, Green Left, accessed at https://web.archive.org/web/20101108234729/http://www.greenleft.org.au/node/11274, Aug. 14, 1996, pp. 2.
Duffus, Heavy-metals—A meaningless term, Chemistry and Human Health Division Clinical Chemistry Section, Commission on Toxicology (2002), 74(5) pp. 793-807.
Fang et al., Lithium chloride-catalyzed selective demethylation of aryl methyl ethers under microwave irradiation, Journal of Molecular Catalysis A: Chemical (Sep. 3, 2007), 274(1-2) p. 16-23.
Klocking and Helbig, Medical aspects and applications of Humic substances accessed at http://www.supremefulvic.com/documents/pdf/5.medical.aspects.and.applications.of.humic.substances.pdf, accessed on Mar. 15, 2016, pp. 2.
Manach et al., Polyphenols: food sources and bioavailability1,2, American Journal of Clinical Nutrition (May 2004), 79(5) pp. 727-747.
Marton and Alder, Carbonyl Groups in Lignin. III. Mild Catalytic Hydrogenation of Björkman Lignin, Acta Chemica Scandinavica (1961), 15(2) pp. 370-383.
Okubo et al., Cell death induced by the phenolic antioxidant tert-butylhydroquinone and its metabolite tert-butylquinone in human monocytic leukemia u937 cells, Food and Chemical toxicology (May 2003), 41(5) pp. 679-688.
Pena-Mendez et al., Humic substances-compounds of still unknown structure: applications in agriculture, industry, environment, and biomedicine, Journal of Applied Biomedicine (Nov. 22, 2004), 3(1) pp. 13-24.
Pettit, Organic Matter, Humus, Humate, Humic Acid, Fulvic Acid and Humin: Their Importance in Soil Fertility and Plant Health, accessed at http://www.humates.com/pdf/ORGANICMATTERPettit.pdf, accessed on Mar. 15, 2016, pp. 17.
Rath et al., Effects of humic acid on broiler chickens, Poultry Science (Mar. 2006), 85(3) pp. 410-414.
Reische et al., Antioxidants, in Food Lipids Chemistry, Nutrition, and Biotechnology, Third edition, CRC press, (1998) pp. 409-433.
Safer and Al-Nughamish, Heptatoxicity induced by the anti-oxidant food additive, butylated hydroxytoluene (BHT), in rates: An electron microscopical study, Histology and Histopatholgly (Apr. 1999), 14(2) pp. 391-406.
Sarafian et al., Synergistic cytotoxicity of Δ9 tetrahydrocannabinol and butylated hydroxyanisole, Toxicology Letters (Jul. 21, 2002), (133) pp. 171-179.
Schneider et al., Inhibition of HIV-1 in Cell Culture by Synthetic Humate Analogues Derived from Hydroquinone: Mechanism of Inhibition, US National Library of Medicine National Institutes of HealthSearch database (Apr. 15, 1996), 218(2) pp. 389-395.
Shahidi and Zhong, Antioxidants: Regulatory Status, in Bailey's Industrial Oil and Fat Products (Mar. 2005), 1(6) Chapter 12, pp. 491-512.
Shahidi et al., Antioxidants, Food Additives Databook (2003), Part 2 pp. 76-83.
Sonnenberg et al., Chemical Degradation of Humic Substances for Structural Characterization, in Aquatic Humic Substances, Chapter 1, Advances in Chemistry (Dec. 15, 1988), (219) pp. 3-23.
Verhagen et al., Butylated hydroxyanisole in perspective, Chemico-Biological Interactions (1991), 80(2) pp. 109-134.
Willard et al., Boron trihalide-methyl sulfide complexes as convenient reagents for dealkylation of aryl ethers, Tetrahedron Letters (1980), 21(39) pp. 3731-3734.
Supplementary European Search Report for European Application No. 13885964.0 mailed on Feb. 10, 2016.
Kucerik et al., Antioxidant effect of lignite humic acids and its salts on the thermo-oxidative stability/degradation of polyvinyl alcohol blends, Environ Chem Lett (2008), 6:241-245.
Hua, Development and Application of Peat Humic Acid in Plastics Industry, HeBei Chemical Engineering (1990), 2:47-48.
Peng et al., Production of Plastics by Regeneration of Humic Acid through Coal Nitration, Chinese Coal (1999), 25(4):39-40.
Zhipei, Plastic Additive, Jian Xi Humic Acid (1985), 1:66.

HUMIC ACID DERIVATIVES AND METHODS OF PREPARATION AND USE

CROSS-REFERENCE TO RELATED APPLICATION

This application is a U.S. national stage filing under 35 U.S.C. §371 of International Application No. PCT/US2013/042814 filed on May 28, 2013 entitled "HUMIC ACID DERIVATIVES AND METHODS OF PREPARATION AND USE," which is incorporated herein by reference in its entirety.

BACKGROUND

Polymers and their composites are the essential materials used in food packaging, medical applications, children toys, teaching aids and other consumer goods. Processing of polymers to the final products by all available technologies require using several types of additives such as stabilizers, plasticizers, fillers, anti-slippage, anti-static charges and others.

The plastics industry is searching for natural additives such as stabilizers, plasticizer, antistatic charges and antioxidants to stabilize polymers used in food packaging and the other applications mentioned above to replace the currently used anti-oxidants like BHT (butylated hydroxy toluene), TBHQ (tertiary butylhydroquinone), BHA (butylated hydroxyl anisole) and synthetic plasticizers such as DOP (dioctyl phthalate).

SUMMARY

New antioxidants for use in food packaging, medical applications, children's toys and teaching aids are ideally non-toxic as they are in direct contact with humans, inexpensive, effective at low concentrations, and able to survive processing such as injection, blow, extrusion or film production. The additives in the finished products can be non-volatile, anti-static and devoid of undesirable color, flavor, and odor effects. The additives can also be compatible with ubiquitous polymer and can be multi-functional additives such as stability effect; being a thermal stabilizer, antioxidant, plasticize, anti-slippage, and anti-static at the same time.

This disclosure details a natural source of inexpensive additives that can be used in food packaging as well as other applications where the plastic materials are in direct contact with humans or other animals. The additives disclosed may function as stabilizers, antioxidants, plasticizers, and/or convey anti-static properties to the end product. The additives are at least inspired by or based on humic acid, its cleaved products and their derivatives such as salts and chelates as a multi-activity stabilizer, antioxidant, chain breaking, free radical scavenger, HCL acceptor for PVC and its copolymers, and an active plasticizer with possible links with aseptic ingredients.

It has been found that subjecting humic acid to selective aryl ether cleavage conditions followed by esterification and chelate formation creates compounds that meet at least one, and sometimes many or all the above described criteria for polymer additives. The stabilization, plasticization and antistatic efficiency of these sustainable natural products and their derivatives is due to their chemical structure which contains all functional groups that are known as antioxidants, free radical scavengers active groups plus having synergistic characteristics via o,p-quinone-hydroquinone structures, HCl deactivating agents for PVC via metal chelates, promising plasticizing agents in addition of being antistatic agents (which prevents dust accumulation) due to high polar phenolic hydroxyl and ester groups. The natural ingredient (humic acid) is currently produced on an industrial scale for various applications. The low molecular weight structures obtained from cleavage of humic acid have tremendous potential as stabilizers, anti-oxidant/thermal stabilizers, plasticizers for various polymer systems, particularly food-safe polymeric packaging, medical applications and children toys, due to their high stabilization efficiency, high decomposition temperature, non-volatility, non-leachability and high chemical stability, natural source, cheap and non-toxic.

The stabilizing compounds are ester derivatives of humic acid I, or ester derivatives of hydrolysis products II, III, and IV of humic acid I. The esters are alkyl esters or substituted alkyl esters of the carboxylic acid moieties of humic acid, or the fatty esters or substituted fatty esters of phenol moieties of humic acid as esters V, VI, VII, and VIII. Various embodiments include chelates and salts of the ester derivatives.

The polymer stabilizing compounds can be prepared by substantially hydrolyzing humic acid to form a mixture of compounds and esterifying at least one functional group of the mixture of compounds to give a polymer stabilizing mixture of compounds. Embodiments of the method further comprise formation of chelates or salts of the compounds. Other embodiments further comprise purification of one or more of the ester components.

Polymeric matrices comprise at least one of the polymer stabilizing compounds. In certain embodiments, the polymeric matrix can be of polyvinyl chloride, low density polyethylene, high density polyethylene, polyvinyl alcohol, polypropylene, or a combination thereof. The polymeric matrix can be used in a food packaging, nutritional product packaging, beverage packaging, toy, medical packaging, or cosmetic packaging.

DETAILED DESCRIPTION

The above summary of the present technology is not intended to describe each illustrated embodiment or every possible implementation of the present technology. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, octyl, decyl, tetradecyl, hexadecyl, eicosyl, tetracosyl and the like. "Cycloalkyl" or "cycloalkyl groups" are branched or unbranched hydrocarbons in which all or some of the carbons are arranged in a ring, such as but not limited to cyclopentyl, cyclohexyl, methylcyclohexyl and the like. The term "lower alkyl" includes an alkyl group of 1 to 6 carbon atoms.

"Substituent" refers to a molecular non-toxic group that replaces a hydrogen in a compound and may include, but is not limited to, $C_1$-$C_{20}$ alkyl. The term "substituted alkyl" is used herein to allow for the presence of one or more additional substituents on an alkyl group.

"Optional" or "optionally" means that the subsequently described event or circumstance may or may not occur, and that the description includes instances where the event occurs and instances where it does not.

The term "halide" as used herein refers to the halogens fluorine, chlorine, bromine, and iodine.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

As used herein the term "transition metal" should be understood to include elements that are non-toxic non heavy metals or radioactive of the Periodic Table. In chemical terms, these are elements having a partially filled inner shell of electrons. The term "transition metal chelate" as used herein generally means a transition metal cation and anions that surround the metal cation and are joined to it by electrostatic bonds.

As used herein, the term "stereoisomer" refers to a compound made up of the same atoms bonded by the same bonds but having different three-dimensional structures which are not interchangeable.

Humic acid having chemical structure (I), wherein

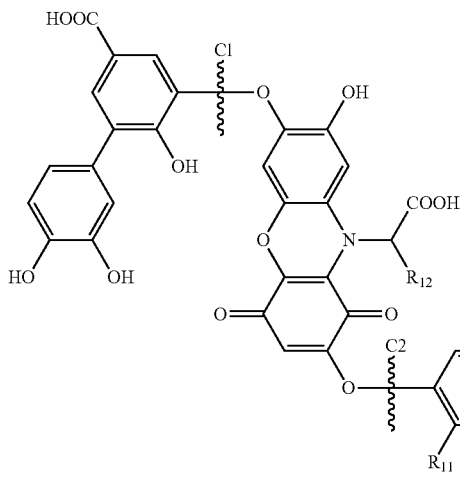
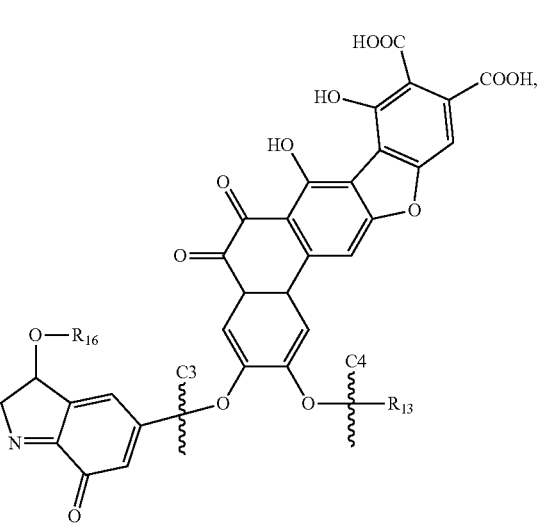

$R_{11}$ is —N($R_{111}$)($R_{112}$), wherein $R_{111}$ is C-acetamido or substituted C-acetamido; $R_{112}$ is hydrogen, —($C_1$-$C_{20}$) alkyl, substituted —($C_1$-$C_{20}$)alkyl, —(C=O)—($C_3$-$C_{19}$)alkyl, or substituted —(C=O)—($C_3$-$C_{19}$)alkyl;

$R_{12}$ is hydrogen, —($C_1$-$C_{20}$)alkyl, or substituted —($C_1$-$C_{20}$)alkyl;

$R_{13}$ is hydrogen, —($C_1$-$C_{20}$)alkyl, substituted —($C_1$-$C_{20}$) alkyl, —(C=O)—($C_3$-$C_{19}$)alkyl, or substituted —(C=O)—($C_3$-$C_{19}$)alkyl; and $R_{16}$ is a hydrogen, glucuronate or substituted glucuronate, has cleavable groups at C1-C4.

Hydrolysis of aryl heteroatom bonds C1—C4 of humic acid I leads to compounds II-IV. The compounds are active multi pH buffers since they dissolve at all pH values. The cleavage derivatives of humic acid at one or more of C1—C4, and their carboxylate salts and chelates have lower molecular weight than humic acid. These derivatives also have high oxygen content due to carboxylate groups adjacent to carbonyl or hydroxyl groups.

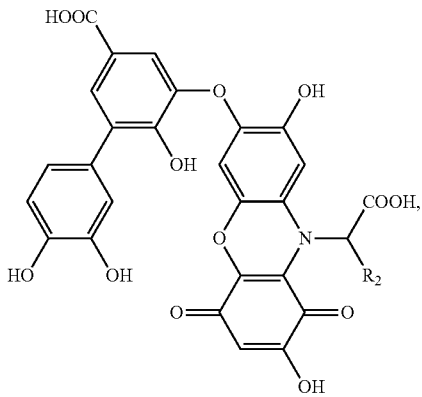

II

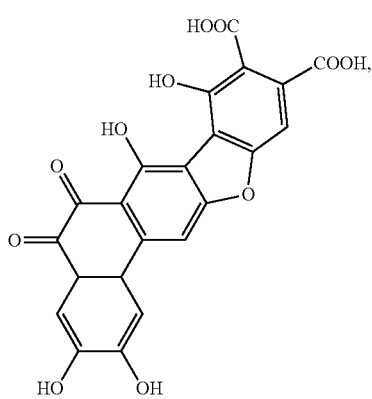

III

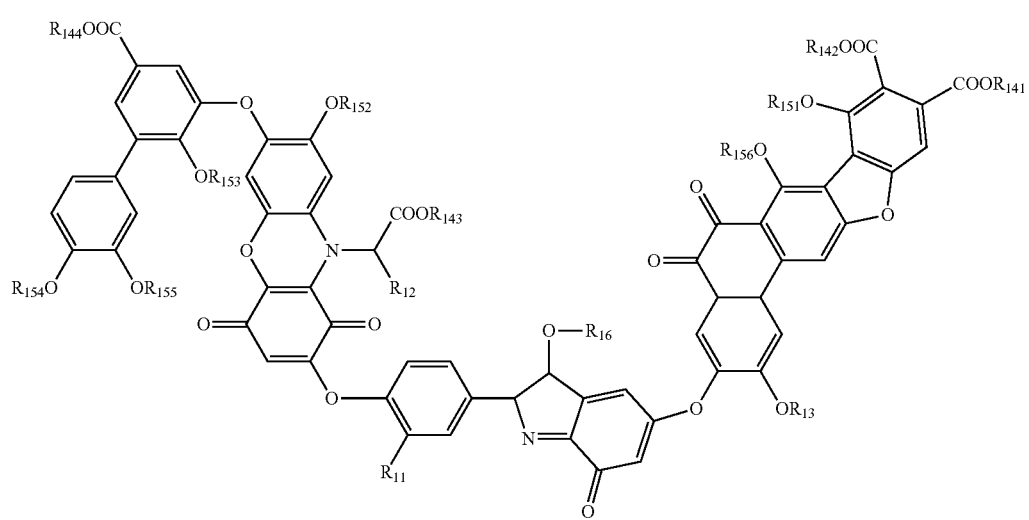

IV salt, or chelate thereof, wherein $R_2$ is hydrogen, —$(C_1$-$C_{20})$alkyl, or substituted —$(C_1$-$C_{20})$alkyl; and $R_4$ is hydrogen, —$(C_1$-$C_{20})$alkyl, or substituted —$(C_1$-$C_{20})$alkyl.

Polymer stabilizing compounds may be prepared as ester derivatives of humic acid I, or ester derivatives of hydrolysis products II, III, and IV of humic acid I. The esters are alkyl esters or substituted alkyl esters of the carboxylic acid moieties, or the fatty esters or substituted fatty esters of phenol moieties of humic acid.

In an aspect, the stabilizing compound is an ester of at least one of formulas V-VIII:

V

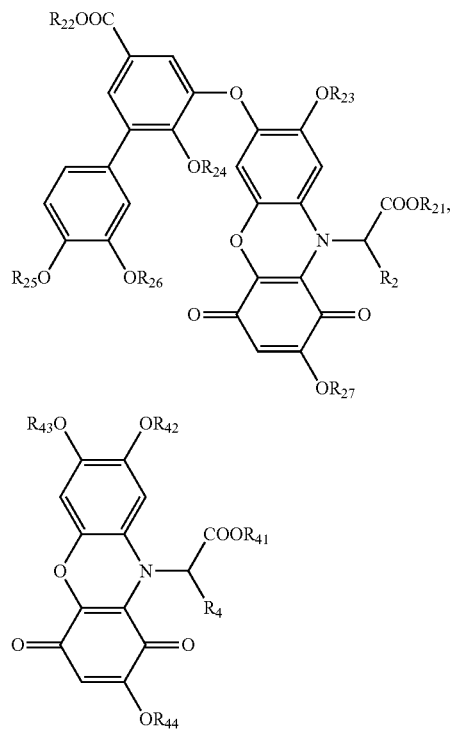
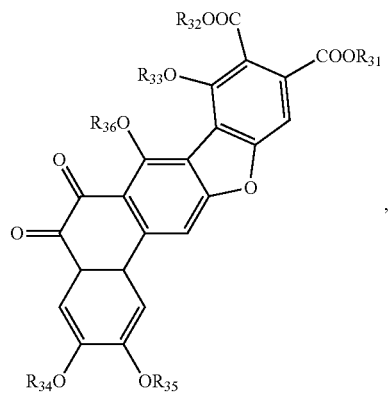

R$_2$ is hydrogen, —(C$_1$-C$_{20}$)alkyl, or substituted —(C$_1$-C$_{20}$)alkyl;

R$_4$ is hydrogen, —(C$_1$-C$_{20}$)alkyl, or substituted —(C$_1$-C$_{20}$)alkyl;

R$_{11}$ is —N(R$_{111}$)(R$_{112}$), wherein R$_{111}$ is C-acetamido or substituted C-acetamido; R$_{112}$ is hydrogen, —(C$_1$-C$_{20}$)alkyl, substituted —(C$_1$-C$_{20}$)alkyl, —(C=O)—(C$_3$-C$_{19}$)alkyl, or substituted —(C=O)—(C$_3$-C$_{19}$)alkyl;

R$_{12}$, R$_{141}$, R$_{142}$, R$_{143}$, and R$_{144}$, are independently hydrogen, —(C$_1$-C$_{20}$)alkyl, or substituted —(C$_1$-C$_{20}$)alkyl;

R$_{13}$ is hydrogen, —(C$_1$-C$_{20}$)alkyl, substituted —(C$_1$-C$_{20}$)alkyl, —(C=O)—(C$_3$-C$_{19}$)alkyl, or substituted —(C=O)—(C$_3$-C$_{19}$)alkyl;

R$_{16}$ is a hydrogen, glucuronate or substituted glucuronate;

R$_{21}$, R$_{22}$, R$_{31}$, R$_{32}$, and R$_{41}$ are independently hydrogen, —(C$_4$-C$_{20}$)alkyl, or substituted —(C$_4$-C$_{20}$)alkyl;

R$_{23}$, R$_{24}$, R$_{25}$, R$_{26}$, R$_{27}$, R$_{33}$, R$_{34}$, R$_{35}$, R$_{36}$, R$_{42}$, R$_{43}$, and R$_{44}$ are independently hydrogen, —(C=O)—(C$_3$-C$_{19}$)alkyl, or substituted —(C=O)—(C$_3$-C$_{19}$)alkyl; and R$_{151}$, R$_{152}$, R$_{153}$, R$_{154}$, R$_{155}$, and R$_{156}$ are independently hydrogen, —(C=O)—(C$_3$-C$_{19}$)alkyl, or substituted —(C=O)—(C$_3$-C$_{19}$)alkyl; and wherein at least one of R$_{141}$, R$_{142}$, R$_{143}$, R$_{144}$, R$_{151}$, R$_{152}$, R$_{153}$, R$_{154}$, R$_{155}$, and R$_{156}$ is not hydrogen; at least one of R$_{21}$, R$_{22}$, R$_{23}$, R$_{24}$, R$_{25}$, R$_{26}$, and R$_{27}$ is not hydrogen; at least one of R$_{31}$, R$_{32}$, R$_{33}$, R$_{34}$, R$_{35}$, and R$_{36}$, is not hydrogen; and at least one of R$_{41}$, R$_{42}$, R$_{43}$, and R$_{44}$ is not hydrogen;

a salt, chelate, or combination thereof.

An embodiment is a compound wherein the compound is at least one chemical formula of VI-VIII, salt, chelate, or combination thereof.

One embodiment is at least one compound with formula V-VIII, wherein the compound is a salt. In another embodiment, the salt is a lithium salt, sodium salt, ammonium salt, potassium salt, calcium salt, barium salt, magnesium salt, manganese salt, zinc salt, aluminum salt, iron salt, or a combination thereof. In yet another embodiment, the salt is a sodium salt, potassium salt, calcium salt, or ammonium salt. In still another embodiment the compound is a polyvalent cation chelate. In another embodiment, the chelate is a calcium, magnesium, iron, or zinc chelate or combination thereof.

Another embodiment is a compound wherein the compound is of chemical formula of VI, salt, chelate, or combination thereof, wherein:

R$_2$ is hydrogen, —(C$_1$-C$_{20}$)alkyl, or substituted —(C$_1$-C$_{20}$)alkyl;

R$_{21}$, R$_{22}$, are independently hydrogen, —(C$_4$-C$_{20}$)alkyl, or substituted —(C$_4$-C$_{20}$)alkyl;

R$_{23}$, R$_{24}$, R$_{25}$, R$_{26}$, and R$_{27}$, are independently hydrogen, —(C=O)—(C$_3$—C$_{19}$)alkyl, or substituted —(C=O)—(C$_3$-C$_{19}$)alkyl; and wherein at least one of R$_{21}$, R$_{22}$, R$_{23}$, R$_{24}$, R$_{25}$, R$_{26}$, and R$_{27}$ is not hydrogen.

Another embodiment is the compound wherein R$_2$ is hydrogen or —(C$_1$-C$_{20}$)alkyl. In certain embodiments, R$_2$ is methyl. In other embodiments, R$_{21}$, R$_{22}$, are independently hydrogen or —(C$_4$-C$_{20}$)alkyl. In other embodiments, wherein R$_{23}$, R$_{24}$, R$_{25}$, R$_{26}$, and R$_{27}$, are independently hydrogen or —(C=O)—(C$_3$-C$_{19}$)alkyl; and wherein at least one of R$_{21}$, R$_{22}$, R$_{23}$, R$_{24}$, R$_{25}$, R$_{26}$, and R$_{27}$ is not hydrogen.

Another embodiment is at least one compound of formula VI, wherein the compound is a salt. In another embodiment, the salt is a lithium salt, sodium salt, ammonium salt, potassium salt, calcium salt, barium salt, magnesium salt, manganese salt, zinc salt, aluminum salt, iron salt, or a combination thereof. In yet another embodiment, the salt is a sodium salt, potassium salt, calcium salt, or ammonium salt. In still another embodiment, at least one compound of formula VI is a polyvalent cation chelate. In another embodiment, the chelate is a calcium, magnesium, iron, or zinc chelate or combination thereof.

Another embodiment the compound has formula VII, salt, chelate, or combination thereof, wherein $R_{31}$, $R_{32}$, are independently hydrogen, —$(C_4-C_{20})$alkyl, or substituted —$(C_4-C_{20})$alkyl;

$R_{33}$, $R_{34}$, $R_{35}$, and $R_{36}$, are independently hydrogen, —(C=O)—$(C_3-C_{19})$alkyl, or substituted —(C=O)—$(C_3-C_{19})$alkyl; and wherein at least one of $R_{31}$, $R_{32}$, $R_{33}$, $R_{34}$, $R_{35}$, and $R_{36}$ is not hydrogen.

Another embodiment is the compound wherein further $R_{31}$ and $R_{32}$, are independently hydrogen or —$(C_4-C_{20})$alkyl, and wherein at least one of $R_{31}$, $R_{32}$, $R_{33}$, $R_{34}$, $R_{35}$, and $R_{36}$ is not hydrogen. Another embodiment is the compound wherein $R_{33}$, $R_{34}$, $R_{35}$, and $R_{36}$ are independently hydrogen or —(C=O)—$(C_3-C_{19})$alkyl, and wherein at least one of $R_{31}$, $R_{32}$, $R_{33}$, $R_{34}$, $R_{35}$, and $R_{36}$ is not hydrogen.

Another embodiment is at least one compound of formula VII, wherein the compound is a salt. In another embodiment, the salt is a lithium salt, sodium salt, ammonium salt, potassium salt, calcium salt, barium salt, magnesium salt, manganese salt, zinc salt, aluminum salt, iron salt, or a combination thereof. In yet another embodiment, the salt is a sodium salt, potassium salt, calcium salt, or ammonium salt. Still another embodiment is at least one compound of formula VII, wherein the compound is a polyvalent cation chelate. In another embodiment, the chelate is a calcium, magnesium, iron, or zinc chelate or combination thereof.

An embodiment is a compound wherein the compound is of chemical formula of VIII, salt, chelate, or combination thereof, wherein $R_4$ is hydrogen, —$(C_1-C_{20})$alkyl, or substituted —$(C_1-C_{20})$alkyl;

$R_{41}$ is independently hydrogen, —$(C_4-C_{20})$alkyl, or substituted —$(C_4-C_{20})$alkyl;

$R_{42}$, $R_{43}$, and $R_{44}$ are independently hydrogen, —(C=O)—$(C_3-C_{19})$alkyl, or substituted —(C=O)—$(C_3-C_{19})$alkyl; and wherein at least one of $R_{41}$, $R_{42}$, $R_{43}$, and $R_{44}$ is not hydrogen.

Another embodiment is the compound wherein further $R_4$ is hydrogen or —$(C_1-C_{20})$alkyl. A certain embodiment is wherein $R_4$ is methyl. Another embodiment is wherein $R_{41}$ is hydrogen or —$(C_4-C_{20})$alkyl, and wherein at least one of $R_{41}$, $R_{42}$, $R_{43}$, and $R_{44}$ is not hydrogen. Still another embodiment is wherein $R_{42}$, $R_{43}$, and $R_{44}$ are independently hydrogen or —(C=O)—$(C_3-C_{19})$alkyl, and wherein at least one of $R_{41}$, $R_{42}$, $R_{43}$, and $R_{44}$ is not hydrogen.

Another embodiment is at least one compound of formula VIII, wherein the compound is a salt. In another embodiment, the salt is a lithium salt, sodium salt, ammonium salt, potassium salt, calcium salt, barium salt, magnesium salt, manganese salt, zinc salt, aluminum salt, iron salt, or a combination thereof. In yet another embodiment, the salt is a sodium salt, potassium salt, calcium salt, or ammonium salt. Still another embodiment is at least one compound of formula VIII, wherein the compound is a polyvalent cation chelate. In another embodiment, the chelate is a calcium, magnesium, iron, or zinc chelate or combination thereof.

Another aspect is a method to prepare a stabilizing compound from humic acid. A representative humic acid (I):

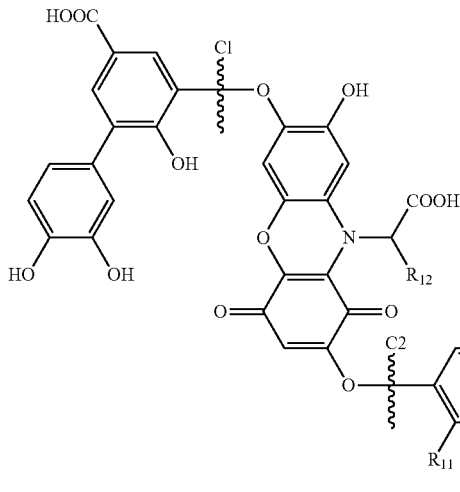
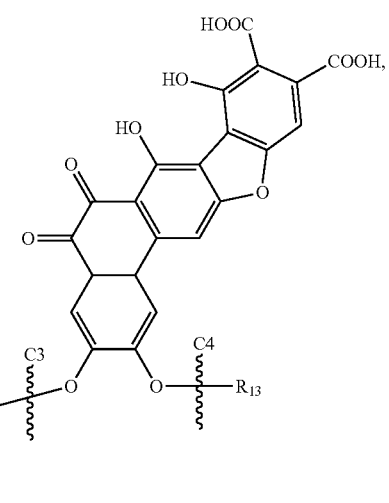

I salt, or chelate thereof, wherein $R_{11}$ is —$N(R_{111})(R_{112})$, wherein $R_{111}$ is C-acetamido or substituted C-acetamido;

$R_{112}$ is hydrogen, —$(C_1-C_{20})$alkyl, substituted —$(C_1-C_{20})$alkyl, —(C=O)—$(C_3-C_{19})$alkyl, or substituted —(C=O)—$(C_3-C_{19})$alkyl;

$R_{12}$ is hydrogen, —$(C_1-C_{20})$alkyl, or substituted —$(C_1-C_{20})$alkyl;

$R_{13}$ is hydrogen, —$(C_1-C_{20})$alkyl, substituted —$(C_1-C_{20})$alkyl, —(C=O)—$(C_3-C_{10})$alkyl, or substituted —(C=O)—$(C_3-C_{19})$alkyl; and $R_{16}$ is a hydrogen, glucuronate or substituted glucuronate.

Is cleaved at C1-C4 to give cleavage products (II-IV):

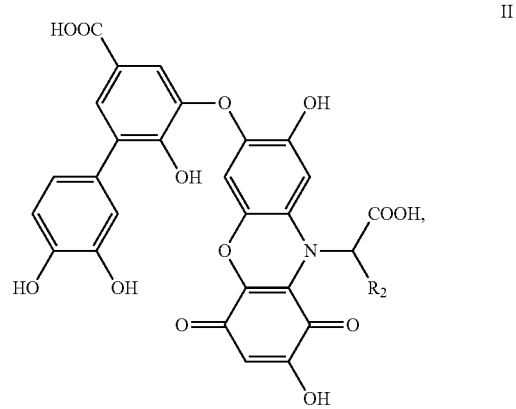

II

-continued

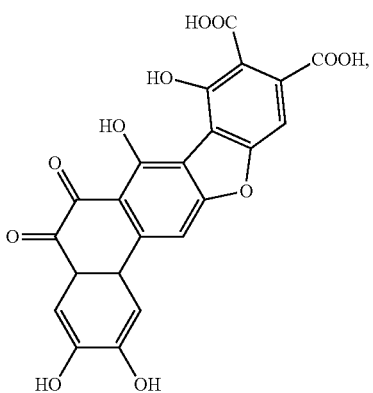

III

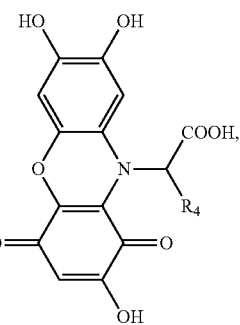

IV salt, or chelate thereof, wherein
R$_2$ is hydrogen, —(C$_1$-C$_{20}$)alkyl, or substituted —(C$_1$-C$_{20}$)alkyl; and
R$_4$ is hydrogen, —(C$_1$-C$_{20}$)alkyl, or substituted —(C$_1$-C$_{20}$)alkyl.

Humic acid I and cleavage products II-IV are contacted with an agent to give fatty acid esters V-VIII.

salt, or chelate thereof, wherein

R$_{11}$ is —N(R$_{111}$)(R$_{112}$), wherein R$_{111}$ is C-acetamido or substituted C-acetamido; R$_{112}$ is hydrogen, —(C$_1$-C$_{20}$)alkyl, substituted —(C$_1$-C$_{20}$)alkyl, —(C=O)—(C$_3$-C$_{19}$)alkyl, or substituted —(C=O)—(C$_3$-C$_{19}$)alkyl;

R$_{12}$, R$_{141}$, R$_{142}$, R$_{143}$, and R$_{144}$ are independently hydrogen, —(C$_1$-C$_{20}$)alkyl, or substituted —(C$_1$-C$_{20}$)alkyl;

R$_{13}$ is hydrogen, —(C$_1$-C$_{20}$)alkyl, substituted —(C$_1$-C$_{20}$)alkyl, —(C=O)—(C$_3$-C$_{10}$)alkyl, or substituted —(C=O)—(C$_3$-C$_{19}$)alkyl;

R$_{151}$, R$_{152}$, R$_{153}$, R$_{154}$, R$_{155}$, and R$_{156}$ are independently hydrogen, —(C=O)—(C$_3$-C$_{10}$)alkyl, or substituted —(C=O)—(C$_3$-C$_{19}$)alkyl; and R$_{16}$ is a hydrogen, glucuronate or substituted glucuronate;

wherein at least one of R$_{141}$, R$_{142}$, R$_{143}$, R$_{144}$, R$_{151}$, R$_{152}$, R$_{153}$, R$_{154}$, R$_{155}$, and R$_{156}$ is not hydrogen;

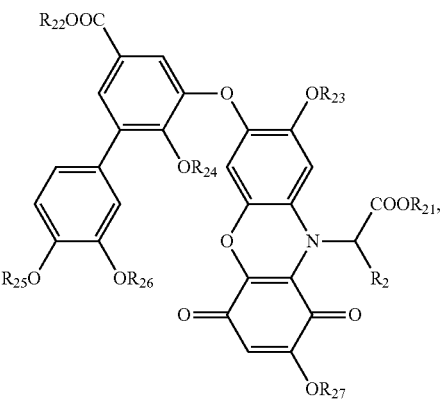

VI

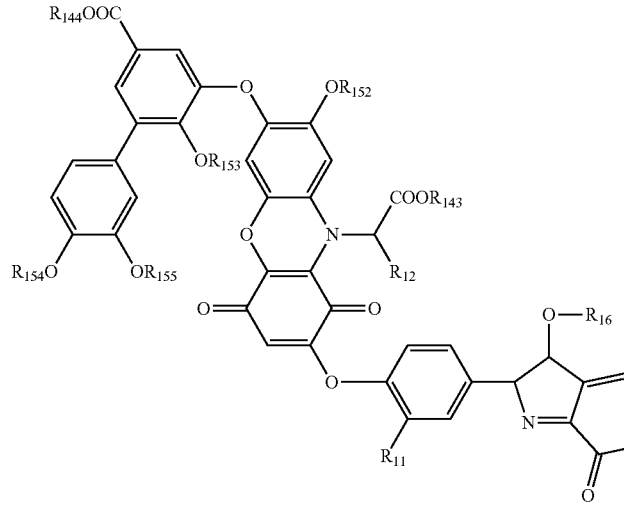

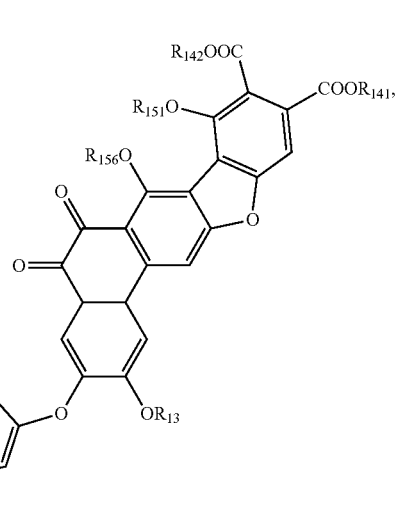

V

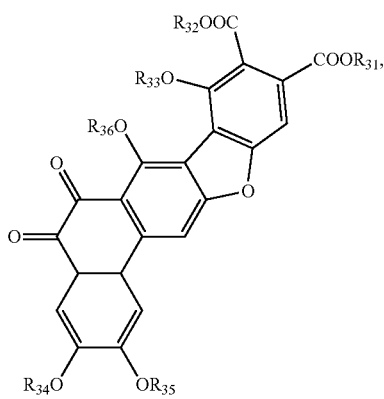

VII

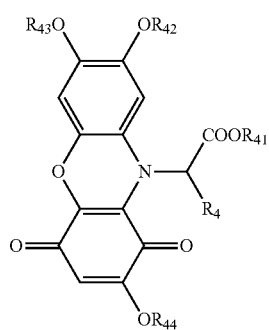

VIII $R_2$ is hydrogen, —($C_1$-$C_{20}$)alkyl, or substituted —($C_1$-$C_{20}$)alkyl;

$R_4$ is hydrogen, —($C_1$-$C_{20}$)alkyl, or substituted —($C_1$-$C_{20}$)alkyl;

$R_{21}$, $R_{22}$, $R_{31}$, $R_{32}$, and $R_{41}$ are independently hydrogen, -($C_4$—$C_{20}$)alkyl, or substituted —($C_4$-$C_{20}$)alkyl;

$R_{23}$, $R_{24}$, $R_{25}$, $R_{26}$, $R_{27}$, $R_{33}$, $R_{34}$, $R_{35}$, $R_{36}$, $R_{42}$, $R_{43}$, and $R_{44}$ are independently hydrogen, —(C=O)—($C_3$-$C_{19}$)alkyl, or substituted —(C=O)—($C_3$-$C_{19}$)alkyl; and wherein at least one of $R_{21}$, $R_{22}$, $R_{23}$, $R_{24}$, $R_{25}$, $R_{26}$, and $R_{27}$ is not hydrogen, at least one of $R_{31}$, $R_{32}$, $R_{33}$, $R_{34}$, $R_{35}$, and $R_{36}$, is not hydrogen, and at least one of $R_{41}$, $R_{42}$, $R_{43}$, and $R_{44}$ is not hydrogen.

In another embodiment the compound has a formula V. In another embodiment, the compound has a formula VI. In yet another embodiment, the compound has a formula VII. In still another embodiment, the compound has a formula VIII.

In the various embodiments, the agent is a reactive fatty acid equivalent, wherein at least one aryl alcohol forms an alkyl ester. In some embodiments, the fatty acid equivalent is an acid chloride. In other embodiments, the fatty acid equivalent is an anhydride. In still other embodiments, the fatty acid is an activated ester. In certain embodiments, the alkyl ester formed is a —(C=O)—($C_3$-$C_{19}$)alkyl fatty ester.

In the various embodiments, the agent is an alcohol, wherein at least one carboxylic acid functionality forms an alkyl ester. In some embodiments, the carboxylic acid is activated as an acid chloride. In other embodiments, the carboxylic acid is activated as an anhydride. In still other embodiments, the carboxylic acid is an activated ester. In yet other embodiments, the carboxylic acid is esterified general acid or base catalysis. In still other embodiments, the alkyl ester is from a transesterification. In certain embodiments, the alkyl ester formed is a —($C_4$-$C_{20}$)alkyl ester.

In the various embodiments, the agent is a first agent and a second agent. In some embodiments, the first agent is an alcohol as above and a second agent is a reactive fatty acid equivalent as above.

In each of the embodiments, the method can further comprise making at least one salt or chelate of the compounds. In an embodiment of the salts, the method comprises making a lithium salt, sodium salt, ammonium salt, potassium salt, calcium salt, barium salt, magnesium salt, manganese salt, zinc salt, aluminum salt, iron salt, or a combination thereof. In yet another embodiment, the method comprises making a sodium salt, potassium salt, calcium salt, or ammonium salt. In an embodiment of the chelates, the method comprises making a polyvalent cation chelate. In another embodiment, the method comprises making a calcium, magnesium, iron, or zinc chelate or combination thereof.

In another embodiment, the method can further comprise isolating at least one compound of formula V-VIII, salt, chelate, or combination thereof. Isolation can include, but is not limited to, filtration, decantation, phase separation, distillation, centrifugation, evaporation, or combinations thereof.

In another embodiment, the method can further comprise purifying at least one compound of formula V-VIII, salt, chelate, or combination thereof. Purification can include, but is not limited to, steam distillation, distillation, crystallization, reverse phase chromatography, normal phase chromatography, precipitation, refining, sublimation, evaporation, extraction, absorption, washing, or combinations thereof.

In various embodiments the humic acid I may be cleaved at positions C1, C2, C3, and C4 by action of a hydrogenolysis cleaving agent. Hydrogenolysis cleaving agents can include, but are not limited to nickel—Catalyzed hydrogenolysis, sodium borohydride ($NaBH_4$), amide hydro halide salts, lithium chloride in dimethylformamide, hydrogen iodide, and hydrogen bromide, and others.

In various embodiments the hydrolysis is carried out in an alkaline solution. In some embodiments, the alkaline solution is an aqueous alkaline hydroxide, or mixtures thereof. In some embodiments, the alkaline solution is aqueous lithium hydroxide, aqueous sodium hydroxide, aqueous potassium hydroxide, or combination thereof. In certain embodiments, the alkaline solution is aqueous sodium hydroxide. In various embodiments, the hydrolysis is performed at a pH of about 8, about 8.5, about 9, about 10, about 11, about 12, about 13, about 14, or at a pH range between or at any of the two pH values. In various embodiments, the hydrolysis is performed with heat. In certain embodiments, the hydrolysis is performed at reflux temperatures.

Still another aspect is a polymeric matrix comprising at least one stabilizing compound of formula V-VIII:

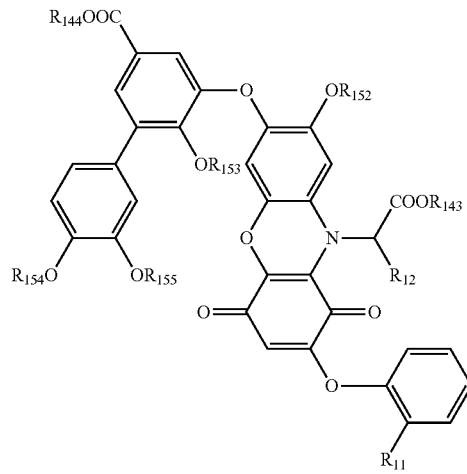

V

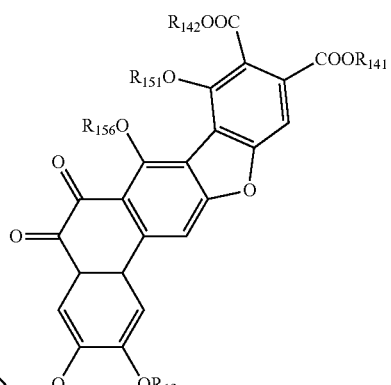

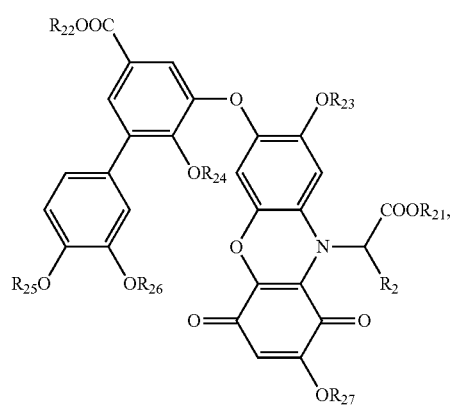

VI

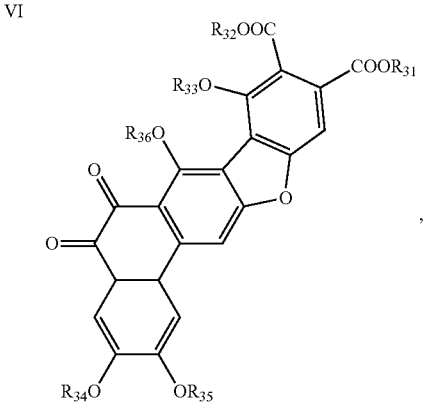

VII

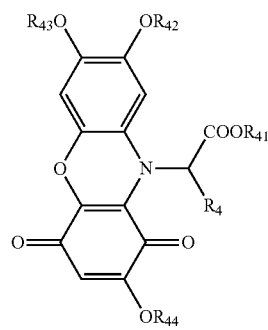

VIII wherein $R_2$ is hydrogen, —$(C_1$-$C_{20})$alkyl, or substituted —$(C_1$-$C_{20})$alkyl;

$R_4$ is hydrogen, —$(C_1$-$C_{20})$alkyl, or substituted —$(C_1$-$C_{20})$alkyl;

$R_{11}$ is —$N(R_{111})(R_{112})$, wherein $R_{111}$ is C-acetamido or substituted C-acetamido; $R_{112}$ is hydrogen, —$(C_1$-$C_{20})$alkyl, substituted —$(C_1$-$C_{20})$alkyl, —(C=O)—$(C_3$-$C_{19})$alkyl, or substituted —(C=O)—$(C_3$-$C_{19})$alkyl;

$R_{12}$, $R_{141}$, $R_{142}$, $R_{143}$, and $R_{144}$ are independently hydrogen, —$(C_1$-$C_{20})$alkyl, or substituted —$(C_1$-$C_{20})$alkyl;

$R_{13}$ is hydrogen, —$(C_1$-$C_{20})$alkyl, substituted —$(C_1$-$C_{20})$alkyl, —(C=O)—$(C_3$-$C_{19})$alkyl, or substituted —(C=O)—$(C_3$-$C_{19})$alkyl;

$R_{16}$ is a hydrogen, glucuronate or substituted glucuronate;

$R_{21}$, $R_{22}$, $R_{31}$, $R_{32}$, and $R_{41}$ are independently hydrogen, -$(C_4$-$C_{20})$alkyl, or substituted —$(C_4$-$C_{20})$alkyl;

$R_{151}$, $R_{152}$, $R_{153}$, $R_{154}$, $R_{155}$, and $R_{156}$ are independently hydrogen, —(C=O)—$(C_3$-$C_{19})$alkyl, or substituted —(C=O)—$(C_3$-$C_{19})$alkyl; and $R_{23}$, $R_{24}$, $R_{25}$, $R_{26}$, $R_{27}$, $R_{33}$, $R_{34}$, $R_{35}$, $R_{36}$, $R_{42}$, $R_{43}$, and $R_{44}$ are independently hydrogen, —(C=O)—$(C_3$-$C_{19})$alkyl, or substituted —(C=O)—$(C_3$-$C_{19})$alkyl; and wherein at least one of $R_{141}$, $R_{142}$, $R_{143}$, $R_{144}$, $R_{151}$, $R_{152}$, $R_{153}$, $R_{154}$, $R_{155}$, and $R_{156}$ is not hydrogen; at least one of $R_{21}$, $R_{22}$, $R_{23}$, $R_{24}$, $R_{25}$, $R_{26}$, and $R_{27}$ is not hydrogen; at least one of $R_{31}$, $R_{32}$, $R_{33}$, $R_{34}$, $R_{35}$, and $R_{36}$, is not hydrogen; and at least one of $R_{41}$, $R_{42}$, $R_{43}$, and $R_{44}$ is not hydrogen; salt, or chelate thereof;

in combination with a polymer.

In an embodiment the compound is at least one compound of formula VI-VIII. In another embodiment the compound has a formula V. In another embodiment, the compound has a formula VI. In yet another embodiment, the compound has a formula VII. In still another embodiment, the compound has a formula VIII.

Embodiments include a polymeric matrix comprising at least one antioxidant compound of formula V-VIII, a salt, or chelate thereof, in combination with a polymer. In certain embodiments, the polymer is a polyvinyl chloride, low density polyethylene, high density polyethylene, polyvinyl alcohol, polypropylene, or combination thereof. In yet other embodiments, the polymeric matrix may be suitable for various packaging to extend a shelf life of a product. In certain embodiments, the polymeric matrix is a food packaging, nutritional product packaging, beverage packaging, toy, medical packaging, or cosmetic packaging.

In yet another embodiment, the antioxidant compound is present in the polymeric matrix by weight at a concentration of about 5%, about 2.5%, about 1%, about 0.5%, about 1000 ppm, about 300 ppm, about 200 ppm, about 100 ppm, about 30 ppm, about 10 ppm, about 3 ppm, about 1 ppm, or any range between two of the concentrations. In various specific embodiments, the antioxidant is present in a polymer at less than about 5000 ppm, less than about 300 ppm, less than about 100 ppm, or less than about 10 ppm. In certain embodiments, the antioxidant compound is between about 0.02% and about 2.5% by weight of the polymer. In another certain embodiment, the antioxidant compound is between about 0.1% and about 0.5% by weight.

In each of the aforementioned embodiments of the polymeric matrix, the antioxidant compound may be a salt. In certain embodiments, the salt is a lithium salt, sodium salt, ammonium salt, potassium salt, calcium salt, barium salt, magnesium salt, manganese salt, zinc salt, aluminum salt, iron salt, or a combination thereof. In certain embodiments, the salt is a sodium salt, potassium salt, calcium salt, ammonium salt, or combination thereof. In an embodiment, the antioxidant compound is a sodium salt. In another embodiment, the antioxidant compound is a potassium salt. In yet another embodiment, the antioxidant compound is a calcium salt. In still another certain embodiment, the antioxidant compound is an ammonium ion salt. In yet other embodiments of the aforementioned antioxidant compounds, the antioxidant compound may be a polyvalent chelate. In certain embodiments, the transition metal ion chelate is a magnesium chelate, calcium chelate, zinc chelate, iron chelate, or combination thereof.

The chelates of fatty ester products V-VIII are particularly suitable as HCl deactivators for PVC and its copolymers. The chelates can react with HCl formed from the thermal decomposition of PVC. The role of HCl is well known to accelerate the thermal decomposition of PVC (accordingly PVC stabilizers consist of HCl deactivators (Scheme 1):

Scheme 1

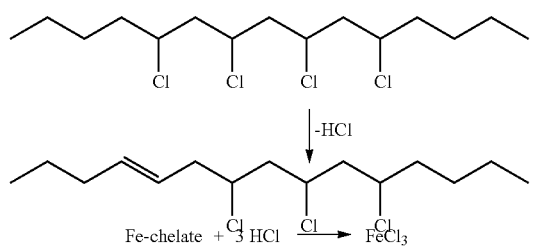

In some embodiments, the fatty ester products V-VIII can be transferred to master batch pellets which can be added to any thermoplastic or elastomers during their processing to the final packaging products. Master batch is a technical method to improve distribution and homogenization of the additives within a polymeric matrix. In a master batch, most of the active ingredients, except the plasticizers, used in small composition ratios such as colorants, stabilizers, antistatic materials and other additives are extruded with a high melt index polymer, for example, either same polymer or from other compatible polymers, and then transferred to a pellet form that which can be easily mixed with the required basic polymer and processed to the final products.

The fatty ester products V-VIII represent ideal structures as antistatic additives which are essential additives usually added to most polymers in order to prevent the accumulation of dusts on the surface of the packaged items such as: toys, medical packaging and appliances and cosmetics which accordingly, leave the surface clean of dust. The efficiency of these materials as anti-static additives is based on the concept that preventing static charge accumulation, by either using conductive materials such as quaternary ammonium salts or by using compounds with highly polar groups that are capable of forming hydrogen bonding or having electrolyte characteristics. The new natural derivatives described in this disclosure possess the characteristics which make packing anti-static: that being they consist of metal chelates and have free hydroxyl groups that form strong hydrogen bonding.

The fatty ester products V-VIII are very efficient multifunctional plasticizing additives and are highly suitable to replace the currently used phthalate plasticizers due to the current global health issues surrounding these plasticizers. The advantage of the new natural based plasticizers over the phthalate plasticizers is that they are non-toxic and based on aromatic structures which give them enhanced compatibility with most common polymers used in thermoplastic industry for packaging. They possess extremely high boiling point and thus are almost non-volatile, and have high molecular weight which leads them to be non-migratable, non-leachable, and have high thermal stability. In other wards it has almost all the requirement of plasticizers for various applications with the added advantage of being non-toxic and food grade as the starting materials are based on natural food ingredient.

A typical esterification reaction of the phenolic groups present in the natural humic antioxidant cleavage product and fatty carboxylic acids such as octanoic acid, iso-octanoic acid, butanoic acid, decanoic acid, or other carboxylic acids with alkyl groups containing: $C_4$ to $C_{20}$. Typical esterification reaction of the carboxylic acids, carboxylic acid anhydride or acid chlorides with phenolic groups present in the natural antioxidant and fatty alcohols such as butyl alcohol, pentyl, hexyl, heptyl, cetyl, to $C_{20}$. The same reactions can be applied to humic acid I, and its cleavage derivatives II-IV to prepare mono, di, tri, or oligo ester groups, and as partially chelated with suitable metal ions.

Cleavage of aryl heteroatom bonds C1-C4 of humic acid I leads to compounds II-IV. The compounds are active multi pH buffers since they dissolve at all pH values. The cleavage derivatives of humic acid at one or more of C1-C4, and their carboxylate salts and chelates have lower molecular weight than humic acid. These derivatives also have high oxygen content due to carboxylate groups adjacent to carbonyl or hydroxyl groups.

Humic acid cleavage derivatives can be obtained by a reductive cleavage technique. Chemical compounds V-VIII, have active functional groups (quinones, hydroquinones and alkyl phenols) that can act as anti-oxidants and free radical scavengers, chelating groups (via carboxyl groups or hydroxyl groups). The chemical compounds V-VIII are less expensive to manufacture than ascorbic acid and have the ability to dissolve and bond minerals and other nutritional elements with enhanced bioavailability.

The anti-oxidation efficiency of these sustainable, natural derivatives is due to their chemical structure which contains functional groups that are known as antioxidants and free radical scavenger active groups. Humic acid as a basic ingredient for the proposed technology is currently extracted on industrial scale mainly for use as organic fertilizers and plant nutrients. It is sourced cheaply from non—Contaminated marsh and forest soils that can contain up to 30-40% humic materials. Furthermore, these compounds have tremendous potential as thermal stabilizers for various polymer systems used in food packaging.

The cleavage derivatives of humic acid I have various uses including as antioxidants for several polymeric systems such as polyvinyl chloride (PVC), polyethylene (PE) and polypropylene (PP). These antioxidants can be used as a solid, solution, chelated with transition (nutrient) metals. The carboxylic acid group can be transformed into carboxylate salts of Na, K, Ca, Zn, Mg, and can form chelates with divalent and trivalent metal ions. The low molecular weight structures derived demonstrate a higher efficiency as anti-oxidants than humic acid I, and the chemical compounds V-VIII have tremendous potential as anti-oxidant/thermal stabilizers for various polymer systems, particularly food-safe polymeric packaging.

The antioxidants of embodiments from cleavage of humic acid typically require no necessary purification steps, such as ultrafiltration or desalination, nor fractionation into fractions with distinct molecular weights and high purity. The crude antioxidant cleavage solution unexpectedly, and advantageously, exhibits high activity without any further costly processing. However, purified compounds, their salts, chelates, and cleavage derivatives can potentially exhibit superior characteristics in certain applications.

Consumer interest in and awareness of the health properties of antioxidants has been increasing in recent years. This has simultaneously increased global sales of antioxidants (whether used as a food preservative or to provide a health enhancing or functional benefit) and foods that are recognized as being naturally rich in antioxidants. As the sector has developed, antioxidants are now being used in the manufacture of a greater variety of goods to cater for increasingly health—Conscious consumers.

The humic acid derivatives are more efficient (based on humic acid studies) and cost effective compared to all other plasticizers and stabilizers. Humic acid derivatives and cleavage derivatives would be cheaper to manufacture than ascorbic acid and synthetic antioxidants and have greater thermal stability convenient for almost all food processing and cooking up to 350° C. and have the ability to dissolve and bond minerals and other nutritional elements with enhanced bioavailability.

EXAMPLES

Although the present technology has been described in considerable detail with reference to certain embodiments thereof, other versions are possible. Therefore the spirit and scope of the appended claims should not be limited to the description and versions contained within this specification. The various aspects of the present technology will be illustrated with reference to the following non-limiting examples.

Example 1

Cleavage of Humic Acid Using Sodium Hypophosphite and Hydrogen Iodide

Humic acid was extracted from non-polluted marsh soils with an organic content of 30-35%. The alkaline extracted humic acid from marsh soils or forests soils was suspended in 25-40% HI solution in a stoichiometric equivalent ratio to the ether groups of humic acid weight ratio of 1:10. The humic acid underwent cleavage in the presence of sodium hypophosphite (10% of the HI) added to prevent further iodination of the aromatic phenolic structures and prevents oxidation of iodine ions.

The reaction mixture was heated to reflux. The humic acid suspension began to cleave after 45 minutes and the solution became colored. The color changed progressively with reflux time. Fractions were taken at 15 minute intervals until all the humic acid suspension disappears (approximately after 10 hours depending on the concentration of HI) until a homogeneous reaction mixture was obtained.

Fraction products were neutralized or transferred to the carboxylate salts (Na, Ca, Mg, Mn, and similar salts) by neutralizing the carboxylic acid groups with required alkaline hydroxides or carbonate.

The reaction matrix compositions mixture were characterized by TLC (Thin Layer Chromatography), pH titration, IR, NMR and molecular weight determination for some of the fractions.

The TLC displayed at least 12 spots using different solvent carriers, indicating the presence of at least 12 compounds in the final reaction mixture. This was in good agreement with the chemical structure evaluation in addition of presence of low aromatic carboxylic acids and hydroquinone derivatives.

Example 2a

Cleavage of Humic Acid Using Nickel Catalysis

The cleavage of bonds of Example 1 may be performed by nickel catalyzed hydrogenolysis. The humic acid is dissolved in 3-octenone or other solvents or mixed solvents in the presence of nickel carbine complex under one bar of hydrogen at a temperature of 80-120° C. The reaction produces a mixture of compounds II-IV.

Example 2b

Cleavage of Humic Acid Using Sodium Borohydride

The cleavage of bonds of Example 1 may be performed by action of sodium borohydride. Humic acid is dissolved in a solution of sodium hydroxide in 1:1 ethanol:water in the presence of Ni—Cr-boride where sodium borohydride is formed in situ. The reaction takes place at atmospheric pressure. The reaction produces a mixture of compounds II-IV.

Example 2c

Cleavage of Humic Acid Using Lithium Chloride

The cleavage of bonds of Example 1 may be performed by action of lithium chloride in dimethyl formamide. Humic acid is dissolved in a solution of LiCl-DMF at boiling conditions for 4-72 hours. The reaction produces a mixture of compounds II-IV.

Example 2d

Cleavage of Humic Acid Using Hydrogen Iodide

The cleavage of bonds of Example 1 may be performed by action of hydrogen iodide. The humic acid is reacted with aqueous hydrogen iodide and sodium hypophosphite to form a suspension. Alternatively, the suspension is heated until a substantially homogeneous reaction mixture is obtained. In yet another alternative, the heating is carried out at reflux temperature. The reaction produces a mixture of compounds II-IV.

Example 2e

Cleavage of Humic Acid Using Hydrogen Bromide

The cleavage of bonds of Example 1 were performed by action of hydrogen bromide. Humic acid was dissolved in an organic solvent such as methyl ethyl ketone or a mixture of solvents, and then this mixture was added to an aqueous solution consisting of glacial acetic acid and concentrated hydrogen bromide at 0-10° C. in the presence of 1% surfactant (Cetrimide). The cleavage was carried out in an emulsion system under efficient mixing for 5 hours. At the end of five hours, the temperature was raised to 25° C. The reaction was continued for an additional hour. The reaction produced a mixture of compounds II-IV.

Example 3a

Esterification of Compounds II-IV Phenols to Give Mixed Nonyl Esters

Mixed acetic-nonanoic anhydride 12.5 gm is added to a 250 ml stirred flask and 0.95 gm of a mixture of compounds II-IV from any one of Examples 1 and 2a-2e and 0.13 gm sulphuric acid added to the anhydride to form a mobile dispersion. This is heated to 90-100° C. and maintained at this temperature for 3 hours before cooling to 40° C. and dispersion in 200 ml of ethanol or petroleum ether. After filtration or concentration the solid is subjected to two further washes before being dried and analyzed to give a yield of 80% of mixed nonyl aryl esters of compounds II-IV.

Example 3b

Esterification of Compound IV Phenols to Give Trinonyl Ester VIII

Mixed acetic-nonanoic anhydride 12.5 gm is added to a 250 ml stirred flask and 3.74 gm 2-(2,7,8-trihydroxy-1,4-dioxo-1H-phenoxazin-10(4H)-yl)propanoic acid (IV, R=Me) and 0.13 gm sulphuric acid added to the anhydride to form a mobile dispersion. This is heated to 90-100° C. and maintained at this temperature for 3 hours before cooling to 40° C. and dispersion in 200 ml of ethanol or petroleum ether. After filtration or concentration the solid is subjected to two further washes before being dried and analyzed to give a yield of 80% of the trinonyl aryl esters of compound IV.

Example 3c

Esterification of Compounds II-IV Carboxylic Acids to Give Mixed Esters

One kg of a mixture of compounds II-IV, 1872 gm of decyl alcohol (12 mol), and 0.59 gm of tetra butyl titanate are weighed into a 4 liter distillation flask with a Dean-Stark-trap and reflux condenser, and heated to boiling under nitrogen. The water of reaction produced during the esterification is regularly removed. After about 3 hours the excess alcohol is distilled off under vacuum. The mixture is cooled to 80° C. and transferred to a 4 liter reaction flask with immersion tube, dropping funnel, and column. A sodium hydroxide solution (5 weight %) is then used for neutralization. The mixture is then heated under vacuum (10 mbar) to 190° C. Deionized water is then added drop-wise via the dropping funnel, at constant temperature. After addition of the water, the heating is switched off and the mixture is cooled. The mixed esters are filtered with a filtration aid to give a mixture of decyl carboxylic esters of compounds VI-VIII.

Example 3d

Esterification of Compound IV Carboxylic Acid to Give Decyl Ester

Compound IV (100 gm), 187 gm of decyl alcohol, and 0.06 gm of tetra butyl titanate are weighed into a 500 mL distillation flask with a Dean-Stark-trap and reflux condenser, and heated to boiling under nitrogen. The water of reaction produced during the esterification is regularly removed. After about 3 hours excess alcohol is distilled off under vacuum. The mixture is cooled to 80° C. and transferred to a 500 mL reaction flask with immersion tube, dropping funnel, and column A sodium hydroxide solution (5 weight %) is then used for neutralization. The mixture is then heated under vacuum (10 mbar) to 190° C. Deionized water is then added drop-wise via the dropping funnel, at constant temperature. After addition of the water, the heating is switched off and the mixture is cooled. The mixed esters are filtered with a filtration aid to form the decyl carboxylic ester of compound VIII.

Example 4a

Preparation of the Calcium Chelates of a Mixture of Decyl Esters of Compounds VI-VIII Calcium oxide (5.6 gm) and 65 gm of the decyl esters of compounds VI-VIII (Example 3c) were placed into a flask provided with a reflux condenser. Ethanol (100 mL) was added and the mixture was stirred and boiled at atmospheric pressure for 5 hours. The reaction mixture was then cooled, and thereafter filtered yielding 65 grams of calcium chelate of the decyl esters having the physical characteristic of a fine white powder.

Example 4b

Preparation of the Magnesium Chelate of Decyl Ester of Compound VIII 4.0 grams (0.1 Mole) of magnesium oxide and 65 grams (0.2 Mole) of the decyl ester of compound VIII (Example 3d) were placed into a flask provided with a reflux condenser. Ethanol (100 mL) was added and the mixture was stirred and boiled at atmospheric pressure for 5 hours. The reaction mixture was then cooled, and thereafter filtered yielding 60 grams of calcium chelate of the decyl ester of compound VIII having the physical characteristic of a fine white powder.

Example 4c

Preparation of the Zinc Chelate of Decyl Ester of Compound VII

Zinc hydroxide is placed in a flask with a reflux condenser and 100 grams of the decyl ester of compound VII. Ethanol is added and the mixture boiled for 3 hours. The mixture is cooled and filtered yielding 100 gm of the zinc chelate of the decyl ester of compound VII.

Example 5

Stability Data

The mixture of the calcium chelate of compounds of formula V, VI, VII, and VIII prepared in Example 4, were evaluated as antioxidants and thermal stabilizers for PVC, low density polyethylene, and polyvinyl alcohol as a model to evaluate the anti-oxidation efficiency using thermal analysis (differential scanning calorimetry (DSC) and thermo gravimetric analysis (TGA)) techniques, including differential thermogravimetry (DTG) to determine the decomposition temperature. The chelates with several transition metal ions showed remarkable efficiency for thermo-oxidative stabilization of PVC. Typical results are provided in Table (1). Tests using 1% of the calcium salt of the hydrolyzed humate mixture in extruded PVC show higher stabilizing efficiency than 1% of humic acid in extruded PVC. Both were better than PVC extruded without an antioxidant.

TABLE (1)

Thermal degradation stability of PVC and stabilized PVCs

| | HCl % (loss) from TGA | | |
|---|---|---|---|
| Temperature, ° C. | PVC control (K value 70) | PVC with 1% Humic acid | PVC with +1% Ca-chelate of a mixture of V, VI, VII, and VIII |
| 250 | 3 | 1 | 0 |
| 260 | 5 | 2 | 0 |
| 270 | 10 | 2 | 0.5 |
| 280 | 33 | 5 | 1.0 |
| 290 | 1 | 13 | 1.0 |
| 300 | 47 | 35 | 5.0 |
| Total HCl loss (%) at Decomp. Temp. | 63 | 57 | 53 |
| Decomp. Temp., ° C., from DTG | 265 | 280 | 310 |
| Rate of decomposition at Decomp. Temp. %/min | 1.63 | 1.09 | 0.73 |

Example 6

Stabilization of Polyethylene for Food Packaging:

Polyethylene films are prepared with 0.1% by weight and with 0.5% by weight of a mixture of the calcium chelate of compounds of formula V, VI, VII, and VIII prepared in Example 4 by extrusion methods to form films for food packaging. The films are subjected to natural sun light in Sydney, Australia, and with high UV light for 4 weeks. The resultant films are tested by IR and UV spectrometry. The films stabilized with metal chelates show no color change and no spectral changes, while unstabilized polyethylene samples as controls show change in coloration and absorption spectra.

Example 7

Stabilization of Polyvinyl Chloride (PVC) for Food Packaging:

PVC (K value 70) stabilized with 1% of a mixture of the calcium chelate of compounds of formula V, VI, VII, and VIII prepared in Example 4 (typical thermal stability characteristics listed in Table 1) are prepared by extrusion to form films for food packaging. The films are subjected to natural sunlight in Sydney, Australia, and with high UV light for 4 weeks. The stabilized films with metal chelates show no color change while control films of unstabilized PVC samples show change in coloration to a dark yellowish color.

What is claimed is:

1. A stabilizing compound comprising a compound of formula V:

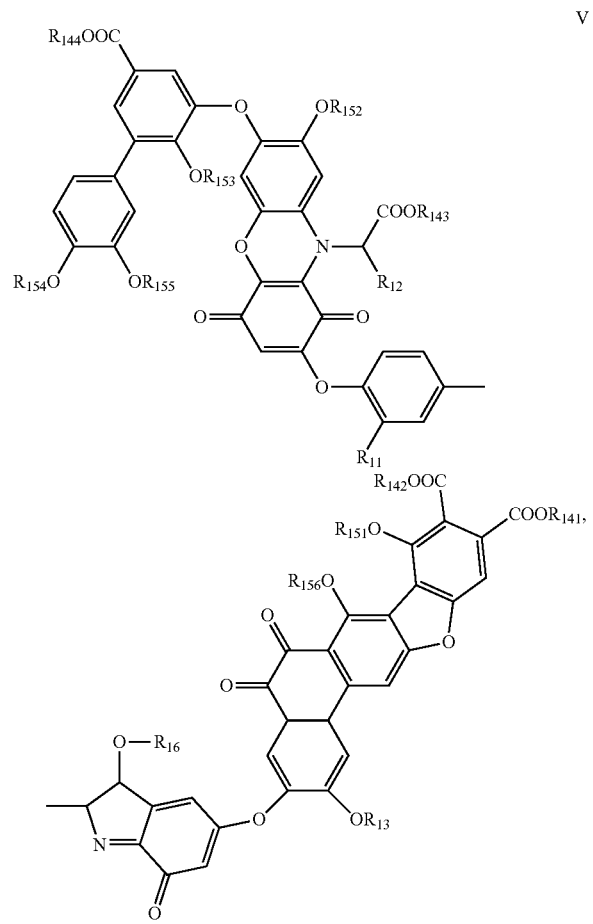

wherein
$R_{11}$ is $-N(R_{111})(R_{112})$, wherein $R_{111}$ is C-acetamido or substituted C-acetamido; $R_{112}$ is hydrogen, $-(C_1-C_{20})$alkyl, substituted $-(C_1-C_{20})$alkyl, $-(C=O)-(C_3-C_{19})$alkyl, or substituted $-(C=O)-(C_3-C_{19})$alkyl;
$R_{12}$, $R_{141}$, $R_{142}$, $R_{143}$, and $R_{144}$ are independently hydrogen, $-(C_1-C_{20})$alkyl, or substituted $-(C_1-C_{20})$alkyl;
$R_{13}$ is hydrogen, $-(C_1-C_{20})$alkyl, substituted $-(C_1-C_{20})$alkyl, $-(C=O)-(C_3-C_{19})$alkyl, or substituted $-(C=O)-(C_3-C_{19})$alkyl;
$R_{16}$ is a hydrogen, glucuronate or substituted glucuronate;
$R_{151}$, $R_{152}$, $R_{153}$, $R_{154}$, $R_{155}$, and $R_{156}$ are independently hydrogen, $-(C=O)-(C_3-C_{19})$alkyl, or substituted $-(C=O)-(C_3-C_{19})$alkyl,
wherein at least one of $R_{141}$, $R_{142}$, $R_{143}$, $R_{144}$, $R_{151}$, $R_{152}$, $R_{153}$, $R_{154}$, $R_{155}$, and $R_{156}$ is not hydrogen;
a salt, chelate, or combination thereof.

2. The compound of claim 1, wherein the compound is a salt thereof.

3. The compound of claim 1, wherein $R_{141}$, $R_{142}$, $R_{143}$, and $R_{144}$ are independently hydrogen or $-(C_4-C_{20})$alkyl.

4. The compound of claim 1, wherein $R_{151}$, $R_{152}$, $R_{153}$, $R_{154}$, $R_{155}$, and $R_{156}$ are independently hydrogen or $-(C=O)-(C_3-C_{19})$alkyl.

5. The compound of claim 1, wherein the compound is a lithium salt, sodium salt, ammonium salt, potassium salt, calcium salt, barium salt, magnesium salt, manganese salt, zinc salt, aluminum salt, iron salt, or a combination thereof.

6. The compound of claim 1, wherein the compound is a polyvalent cation chelate.

7. The compound of claim 1, wherein the compound is a calcium chelate, magnesium chelate, iron chelate, or zinc chelate or combination thereof.

8. A method of preparing a polymer stabilizing mixture of compounds, the method comprising:
substantially hydrolyzing a humic acid to form a mixture of compounds according to formula V a salt or chelate thereof:

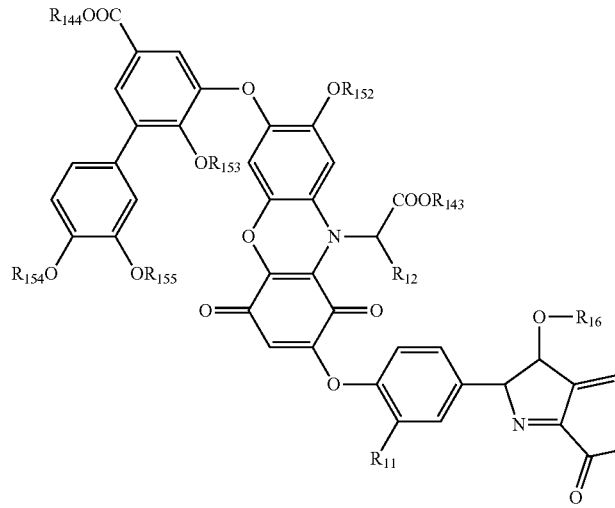
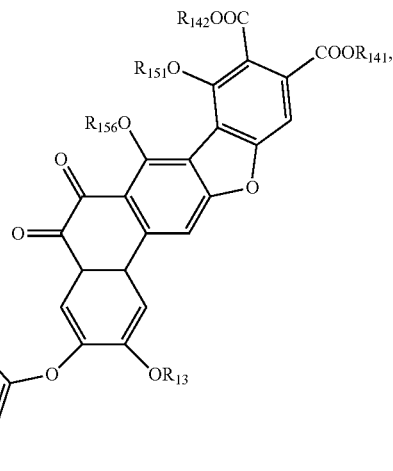

V wherein:
- $R_{11}$ is —N($R_{111}$)($R_{112}$), wherein $R_{111}$ is C-acetamido or substituted C-acetamido;
- $R_{112}$ is hydrogen, —($C_1$-$C_{20}$)alkyl, substituted —($C_1$—$C_{20}$)alkyl, —(C=O)—($C_3$-$C_{19}$ alkyl, or substituted —(C=O)—($C_3$-$C_{19}$)alkyl;
- $R_{12}$, $R_{141}$, $R_{142}$, $R_{143}$ and $R_{144}$ are independently hydrogen, -($C_4$—$C_{20}$)alkyl, or substituted —($C_4$-$C_{20}$ alkyl;
- $R_{13}$ is hydrogen, —($C_1$-$C_{20}$ alkyl, substituted —($C_1$-$C_{20}$) alkyl, —(C=O)—($C_3$—$C_{19}$ )alkyl, or substituted —(C=O)—($C_3$-$C_{19}$)alkyl;
- $R_{16}$ is hydrogen, glucuronate, or substituted glucuronate;
- $R_{151}$, $R_{152}$, $R_{153}$, $R_{154}$, $R_{155}$, and $R_{156}$ are independently hydrogen, —(C=O)—($C_3$-$C_{19}$)alkyl, or substituted —(C=O)—($C_3$-$C_{19}$)alkyl;
- $R_{141}$, $R_{142}$, $R_{143}$, $R_{144}$, $R_{151}$, $R_{152}$, $R_{153}$, $R_{154}$, $R_{155}$, and $R_{156}$ are hydrogen; and esterifying at least one functional group of the mixture of compounds to give a polymer stabilizing mixture of compounds.

9. The method of claim 8, further comprising forming a chelate of the compound of the polymer stabilizing mixture with a calcium cation, magnesium cation, zinc cation, iron cation, or combinations thereof.

10. The method of claim 8, further comprising forming a salt of the compound of the polymer stabilizing mixture to form a lithium salt, sodium salt, ammonium salt, potassium salt, calcium salt, barium salt, magnesium salt, manganese salt, zinc salt, aluminum salt, iron salt, or a combination thereof.

11. The method of claim 8, further comprising purifying the compound of the polymer stabilizing mixture.

12. The method of claim 8, further comprising isolating the compound of formula V wherein at least one of $R_{141}$, $R_{142}$, $R_{143}$, $R_{144}$, $R_{151}$, $R_{152}$, $R_{153}$, $R_{154}$, $R_{155}$, and $R_{156}$ is not hydrogen; at least one of $R_{21}$, $R_{22}$, $R_{23}$, $R_{24}$, $R_{25}$, $R_{26}$, and $R_{27}$ is not hydrogen; at least one of $R_{31}$, $R_{32}$, $R_{33}$, $R_{34}$, $R_{35}$, and $R_{36}$ is not hydrogen; and at least one of $R_{41}$, $R_{42}$, $R_{43}$, and $R_{44}$ is not hydrogen.

13. The method of claim 8, wherein the humic acid comprises at least one compound of formula I:

I

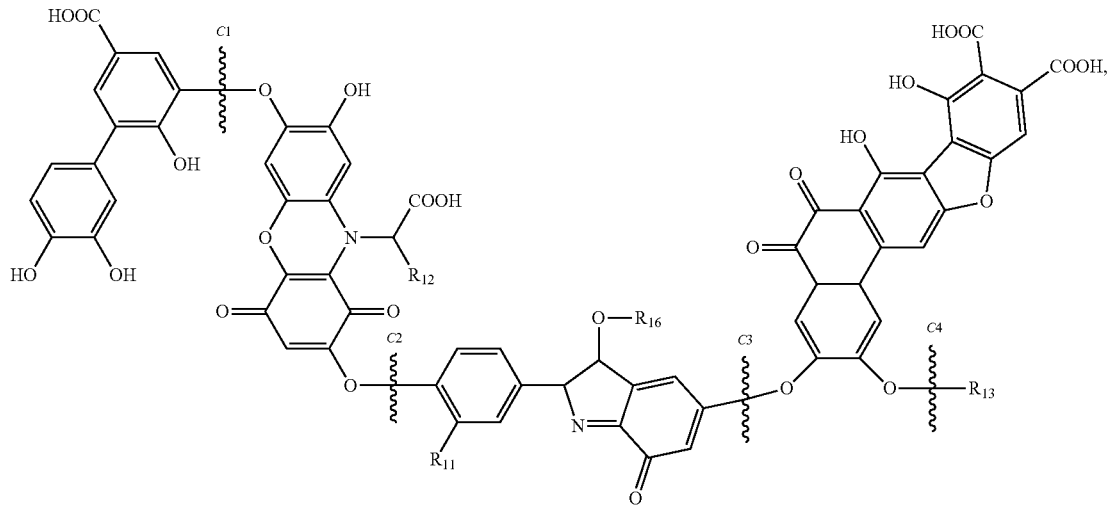

salt, or chelate thereof, wherein
$R_{11}$ is —$N(R_{111})(R_{112})$, wherein $R_{111}$ is C-acetamido or substituted C-acetamido; $R_{112}$ is hydrogen, —$(C_1-C_{20})$alkyl, substituted —$(C_1-C_{20})$alkyl, —(C=O)—$(C_3-C_{19})$alkyl, or substituted —(C=O)—$(C_3-C_{19})$alkyl;

$R_{12}$ is hydrogen, —$(C_1-C_{20})$alkyl, or substituted —$(C_1-C_{20})$alkyl;

$R_{13}$ is hydrogen, —$(C_1-C_{20})$alkyl, substituted —$(C_1-C_{20})$alkyl, —(C=O)—$(C_3-C_{19})$alkyl, or substituted —(C=O)—$(C_3-C_{19})$alkyl; and $R_{16}$ is a hydrogen, glucuronate or substituted glucuronate.

14. The method of claim 8, wherein the hydrolyzing comprises hydrolyzing in the presence of an alkaline solution.

15. The method of claim 14, wherein the alkaline solution is aqueous lithium hydroxide, aqueous sodium hydroxide, aqueous potassium hydroxide, or combination thereof.

16. The method of claim 8, wherein the hydrolyzing comprises hydrolyzing at a pH of 8.5-13.

\* \* \* \* \*

UNITED STATES PATENT AND TRADEMARK OFFICE
CERTIFICATE OF CORRECTION

PATENT NO. : 9,556,134 B2  
APPLICATION NO. : 14/894660  
DATED : January 31, 2017  
INVENTOR(S) : Adam et al.

Page 1 of 1

It is certified that error appears in the above-identified patent and that said Letters Patent is hereby corrected as shown below:

In the Specification

Column 1, Line 8, delete "§371" and insert -- § 371 --, therefor.

Column 10, Line 44, delete "-(C=O)-($C_3$-$C_{10}$)alkyl," and insert -- -(C=O)-($C_3$-$C_{19}$)alkyl, --, therefor.

Column 12, Line 11, delete "-(C=O)-($C_3$-$C_{10}$)alkyl," and insert -- -(C=O)-($C_3$-$C_{19}$)alkyl, --, therefor.

Column 12, Line 15, delete "-(C=O)-($C_3$-$C_{10}$)alkyl," and insert -- -(C=O)-($C_3$-$C_{19}$)alkyl, --, therefor.

In the Claims

Column 25, Line 31, Claim 8, delete "-(C=O)-($C_3$-$C_{19}$ alkyl," and insert -- -(C=O)-($C_3$-$C_{19}$)alkyl, --, therefor.

Column 25, Line 33, Claim 8, delete "$R_{143}$ and" and insert -- $R_{143,}$ and --, therefor.

Column 25, Line 34, Claim 8, delete "-($C_4$-$C_{20}$ alkyl;" and insert -- -($C_4$-$C_{20}$)alkyl; --, therefor.

Column 25, Line 35, Claim 8, delete "-($C_1$-$C_{20}$ alkyl," and insert -- -($C_1$-$C_{20}$)alkyl, --, therefor.

Signed and Sealed this  
Fourth Day of April, 2017

Michelle K. Lee  
*Director of the United States Patent and Trademark Office*